(12) United States Patent
Swamy et al.

(10) Patent No.: US 10,138,190 B2
(45) Date of Patent: Nov. 27, 2018

(54) PROCESS FOR PREPARATION OF OSPEMIFENE

(71) Applicant: Glenmark Pharmaceuticals Limited, Mumbai (IN)

(72) Inventors: Veerabhadra Swamy, Bangalore (IN); Kumar Hari Bhushan, Gurgaon (IN); Shekhar Bhaskar Bhirud, Mumbai (IN); Dilipkumar Jibhau Patil, Nasik (IN); Eknath Kundlik Khemnar, Ahmednagar (IN)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 0 days.

(21) Appl. No.: 15/541,536

(22) PCT Filed: Jan. 6, 2016

(86) PCT No.: PCT/IB2016/050046
§ 371 (c)(1),
(2) Date: Jul. 5, 2017

(87) PCT Pub. No.: WO2016/110805
PCT Pub. Date: Jul. 14, 2016

(65) Prior Publication Data
US 2018/0022674 A1  Jan. 25, 2018

(30) Foreign Application Priority Data
Jan. 9, 2015  (IN) .............. 88/MUM/2015

(51) Int. Cl.
| | | |
|---|---|---|
| *C07C 37/86* | (2006.01) |
| *B01J 23/44* | (2006.01) |
| *C07C 37/84* | (2006.01) |
| *C07C 41/18* | (2006.01) |
| *C07C 41/22* | (2006.01) |
| *C07C 37/00* | (2006.01) |
| *C07C 41/16* | (2006.01) |
| *C07C 41/26* | (2006.01) |
| *C07C 41/30* | (2006.01) |

(52) U.S. Cl.
CPC .............. *C07C 37/86* (2013.01); *B01J 23/44* (2013.01); *C07C 37/00* (2013.01); *C07C 37/84* (2013.01); *C07C 41/16* (2013.01); *C07C 41/18* (2013.01); *C07C 41/22* (2013.01); *C07C 41/26* (2013.01); *C07B 2200/09* (2013.01); *C07B 2200/13* (2013.01); *C07C 41/30* (2013.01)

(58) Field of Classification Search
CPC ......... C07C 37/86; C07C 41/18; C07C 41/22; C07C 37/84; B01J 23/44; C07B 2200/09; C07B 2200/13
See application file for complete search history.

(56) References Cited

U.S. PATENT DOCUMENTS

| | | | |
|---|---|---|---|
| 4,219,683 A * | 8/1980 | Wu ...................... B01J 23/44 568/812 |
| 4,996,225 A | 2/1991 | Toivola et al. |
| 5,912,273 A | 6/1999 | Degregorio et al. |
| 2005/0187301 A1 | 8/2005 | Lehtola et al. |
| 2011/0015448 A1 | 1/2011 | Sodervall et al. |
| 2013/0035514 A1 | 2/2013 | Eklund et al. |
| 2015/0274624 A1 | 10/2015 | Tois et al. |
| 2015/0321983 A1 | 11/2015 | Tois |

FOREIGN PATENT DOCUMENTS

| | | | |
|---|---|---|---|
| CN | 103242142 A | 8/2013 | |
| WO | WO 9732574 | * 9/1997 | ........... A61K 31/085 |

* cited by examiner

*Primary Examiner* — Rosalynd A Keys
(74) *Attorney, Agent, or Firm* — Ryan, Mason & Lewis, LLP

(57) ABSTRACT

The present invention relates to a process for the preparation of ospemifene and pharmaceutically acceptable salts thereof which comprises the step of recycling the undesired E-4-(4-hydroxy-1,2-diphenylbut-1-enyl)phenol to generate an isomeric mixture of Z,E-4-(4-hydroxy-1,2-diphenylbut-1-enyl)phenol.

14 Claims, 1 Drawing Sheet

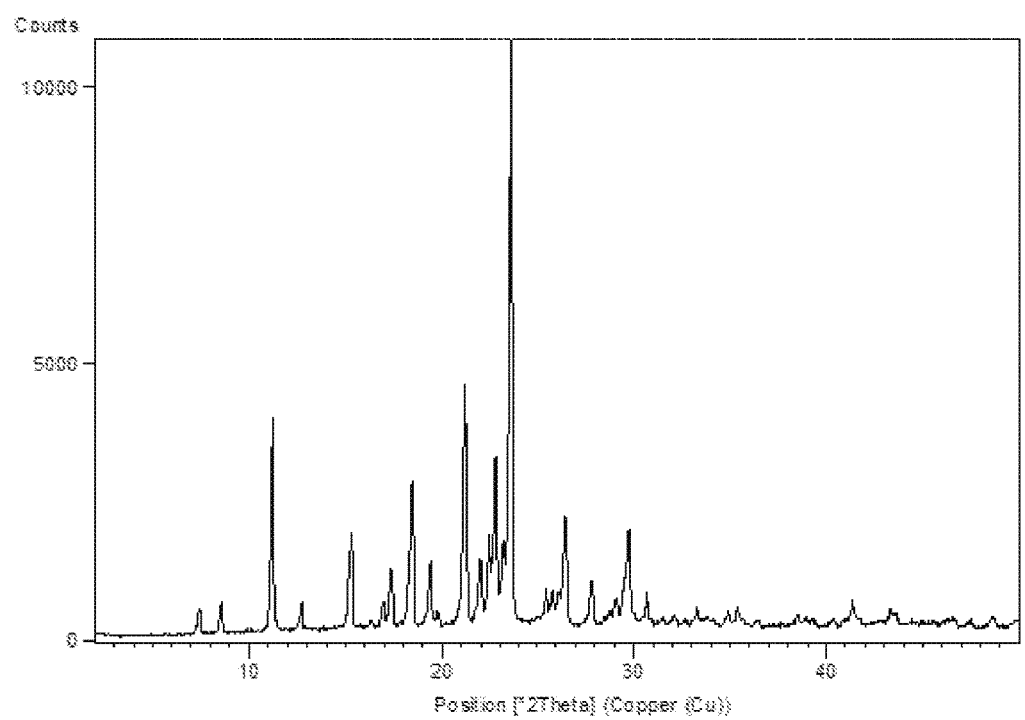

PROCESS FOR PREPARATION OF OSPEMIFENE

PRIORITY

This application claims priority under 35 U.S.C. § 371 to International Application No. PCT/IB2016/050046, filed Jan. 6, 2016 which claims the benefit of Indian Provisional Application 88/MUM/2015 filed Jan. 9, 2015, and entitled "PROCESS FOR PREPARATION OF OSPEMIFENE", the contents of which are incorporated herein by reference.

BACKGROUND OF THE INVENTION

Technical Field

The present invention relates to a process for the preparation of ospemifene and pharmaceutically acceptable salts thereof which comprises the step of recycling the undesired E-4-(4-hydroxy-1,2-diphenylbut-1-enyl)phenol to generate an isomeric mixture of Z,E-4-(4-hydroxy-1,2-diphenylbut-1-enyl)phenol.

Description of the Related Art

Ospemifene, also known as Z-2-[4-(4-chloro-1,2-diphenylbut-1-enyl)phenoxy]ethanol, is represented by the structure of formula I.

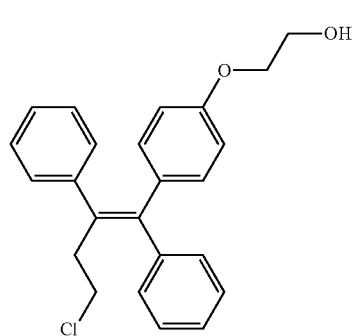

Ospemifene is an estrogen agonist/antagonist indicated for the treatment of moderate to severe dyspareunia, a symptom of vulvar and vaginal atrophy, due to menopause. Ospemifene is marketed under the brand name OSPHENA® in the United States.

There is no teaching in the art for the preparation of ospemifene wherein the undesired intermediate E-4-(4-hydroxy-1,2-diphenylbut-1-enyl)phenol formed as a by-product, is recycled for increasing the productivity of the desired Z-isomer which is used for preparing ospemifene.

There is a need in the art, therefore, for a cost-effective synthesis of ospemifene, which would be advantageous over the reported processes known in the art.

The object of the present invention is to provide a process for the preparation of ospemifene comprising recycling the undesired E-4-(4-hydroxy-1,2-diphenylbut-1-enyl)phenol to generate an isomeric mixture of Z,E-4-(4-hydroxy-1,2-diphenylbut-1-enyl)phenol, isomeric separation of the desired Z-isomer from the Z,E-mixture, optionally repeating the recycling and isomeric separation steps and converting the desired Z-isomer to ospemifene.

SUMMARY OF THE INVENTION

In one aspect, the present invention provides a process for the preparation of ospemifene, a compound of formula I,

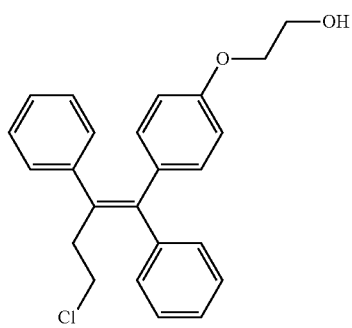

and pharmaceutically acceptable salts thereof, the process comprising:

(a) providing an isomeric mixture of Z,E-4-(4-hydroxy-1,2-diphenylbut-1-enyl)phenol;

(b) separating the desired Z-isomer, a compound of formula IIa, or a salt thereof and the undesired E-isomer, a compound of formula IIb, or a salt thereof from the isomeric mixture of Z,E-4-(4-hydroxy-1,2-diphenylbut-1-enyl)phenol;

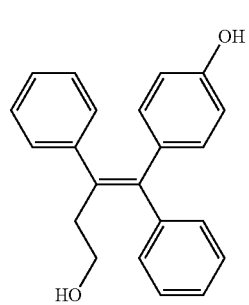

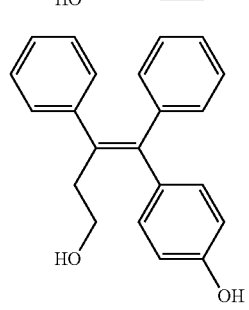

(c) recycling the undesired E-isomer, the compound of formula IIb, or a salt thereof to generate an isomeric mixture of Z,E-4-(4-hydroxy-1,2-diphenylbut-1-enyl)phenol;

(d) optionally, repeating steps (b) and (c); and (e) converting the Z-isomer of 4-(4-hydroxy-1,2-diphenylbut-1-enyl)phenol, the compound of formula IIa, or a salt thereof obtained in step (b) to ospemifene.

In another embodiment, the present invention provides a process for the preparation of ospemifene, having a particle size distribution wherein the $D_{50}$ particle size is in the range of about 15 microns to about 75 microns and the $D_{90}$ particle size is in the range of 50 microns to about 150 microns, the process comprising:

(a) providing a solution of ospemifene in a solvent selected from alcohols, nitriles, water, or mixture thereof;
(b) precipitating out ospemifene from the solution obtained in step (a); and
(c) isolating the solid formed in step (b) to give ospemifene, having a $D_{50}$ particle size in the range of about 15 microns to about 75 microns and $D_{90}$ particle size in the range of 50 microns to about 150 microns.

BRIEF DESCRIPTION OF THE DRAWINGS

FIG. 1 is a characteristic XRPD of ospemifene as obtained in Example 10.

DETAILED DESCRIPTION OF THE INVENTION

The present invention provides a process for the preparation of ospemifene, a compound of formula I,

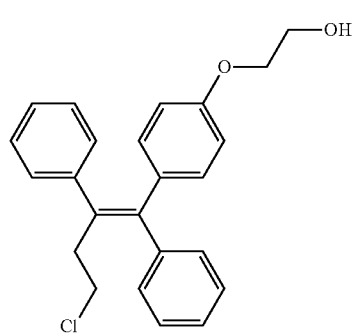

and pharmaceutically acceptable salts thereof, the process comprising:
(a) providing an isomeric mixture of Z,E-4-(4-hydroxy-1,2-diphenylbut-1-enyl)phenol;
(b) separating the desired Z-isomer, a compound of formula IIa, or a salt thereof and the undesired E-isomer, a compound of formula IIb, or a salt thereof from the isomeric mixture of Z,E-4-(4-hydroxy-1,2-diphenylbut-1-enyl)phenol;

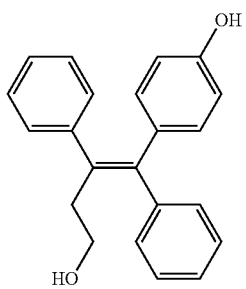

IIa

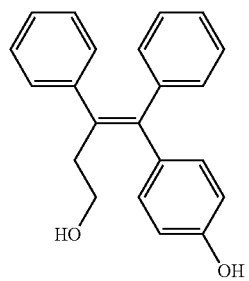

IIb (c) recycling the undesired E-isomer, the compound of formula IIb, or a salt thereof to generate an isomeric mixture of Z,E-4-(4-hydroxy-1,2-diphenylbut-1-enyl)phenol;
(d) optionally, repeating steps (b) and (c); and
(e) converting the Z-isomer of 4-(4-hydroxy-1,2-diphenylbut-1-enyl)phenol, the compound of formula IIa, or a salt thereof obtained in step (b) to ospemifene.

In the present application, the term "room temperature" means a temperature of about 25° C. to about 30° C.

In (a) of the process for the preparation of ospemifene, a compound of formula I, an isomeric mixture of Z,E-4-(4-hydroxy-1,2-diphenylbut-1-enyl)phenol is prepared as schematically represented by Scheme I.

Scheme I

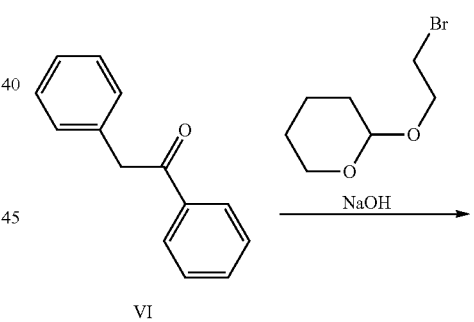

VI

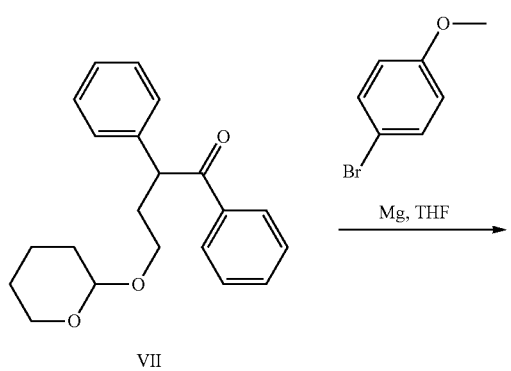

VII

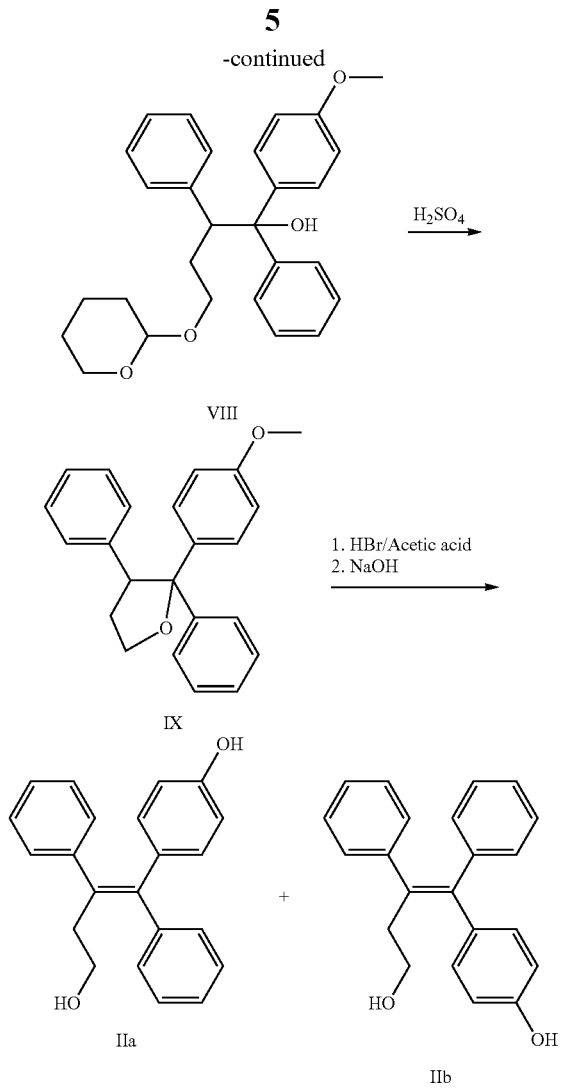

In (b) of the process for the preparation of ospemifene, a compound of formula I, the desired Z-isomer, a compound of formula IIa, or a salt thereof and the undesired E-isomer, a compound of formula IIb, or a salt thereof are separated from the isomeric mixture of Z,E-4-(4-hydroxy-1,2-diphenylbut-1-enyl)phenol, the process comprising:

(i) subjecting the isomeric mixture of Z,E-4-(4-hydroxy-1,2-diphenylbut-1-enyl)phenol to treatment with a base in a solvent to generate a reaction mixture;

(ii) separating the desired Z-isomer, the compound of formula IIa, or a salt thereof and the undesired E-isomer, the compound of formula IIb, or a salt thereof from the reaction mixture obtained in step (i); and (iii) optionally, treating the separated Z-isomer, the compound of formula IIa, or a salt thereof and the E-isomer, the compound of formula IIb, or a salt thereof with an acid.

In (i) of the above process, the isomeric mixture of Z,E-4-(4-hydroxy-1,2-diphenylbut-1-enyl)phenol is subjected to treatment with a base in a solvent to generate a reaction mixture.

The suitable base includes, but is not limited to alkali metal hydroxides such as lithium hydroxide, sodium hydroxide, potassium hydroxide; alkaline earth metal hydroxides; alkali metal hydrides such as sodium hydride, potassium hydride; alkali metal alcoholates such as lithium methoxide, sodium methoxide, potassium methoxide, rubidium methoxide, caesium methoxide, lithium ethoxide, sodium ethoxide, potassium ethoxide, sodium pentoxide, lithium tert-butoxide, sodium tert-butoxide, potassium tert-butoxide; alkaline earth metal alcoholates such as calcium ethoxide, magnesium iso-propoxide. Preferably the base selected is sodium hydroxide.

A suitable solvent includes but is not limited to ketones such as acetone, ethyl methyl ketone, methyl isobutyl ketone and the like; haloalkanes such as dichloromethane, chloroform, ethylene dichloride, and the like; alcohols such as methanol, ethanol, 1-propanol, 2-propanol, 1-butanol, 2-butanol, 1-pentanol, 1-octanol and the like; esters such as methyl acetate, ethyl acetate, n-propyl acetate, isopropyl acetate, tert-butyl acetate and the like; hydrocarbons such as toluene, xylene, chlorobenzene, heptane, hexane and the like; ethers such as diethyl ether, diisopropyl ether, methyl tert-butyl ether, tetrahydrofuran, dioxane and the like; dimethyl formamide, dimethyl sulfoxide; dimethyl acetamide; water; or mixtures thereof. Preferably the solvent selected is acetone, acetone-water mixture.

In (ii) of the above process, the desired Z-isomer, the compound of formula IIa, or a salt thereof and the undesired E-isomer, the compound of formula IIb, or a salt thereof are separated from the reaction mixture obtained in step (i), by any of the following:

(x) by carrying out step (i) in a solvent in which one of the isomers, or salt thereof is soluble and the other isomer, or salt thereof is insoluble and precipitated out; or (y) by carrying out step (i) in a solvent and by adding an anti-solvent to it wherein one of the isomers, or salt thereof is precipitated out; or (z) by removing the solvent of step (i) and adding a second solvent to it in which one of the isomers, or salt thereof is soluble and the other isomer, or salt thereof is insoluble and precipitated out.

In one embodiment, the Z-isomer, the compound of formula IIa, or salt thereof is selectively separated from the E-isomer, the compound of formula IIb, or salt thereof by being soluble in the solvent and the E-isomer, or salt thereof being insoluble and precipitated out in the solvent.

In one embodiment, the Z-isomer, the compound of formula IIa, or salt thereof is selectively separated from the E-isomer, the compound of formula IIb, or salt thereof by being insoluble and precipitated out in the solvent and the E-isomer, or salt thereof being soluble in the solvent.

In one embodiment, the Z-isomer, the compound of formula IIa, or salt thereof is selectively separated from the E-isomer, the compound of formula IIb, or salt thereof by addition of a suitable anti-solvent wherein one of the isomers, or salt thereof is precipitated out.

A suitable anti-solvent includes but is not limited to ketones such as acetone, ethyl methyl ketone, methyl isobutyl ketone and the like; haloalkanes such as dichloromethane, chloroform, ethylene dichloride, and the like; alcohols such as methanol, ethanol, 1-propanol, 2-propanol, 1-butanol, 2-butanol, 1-pentanol, 1-octanol and the like; esters such as methyl acetate, ethyl acetate, n-propyl acetate, isopropyl acetate, tert-butyl acetate and the like; hydrocarbons such as toluene, xylene, chlorobenzene, heptane, hexane and the like; ethers such as diethyl ether, diisopropyl ether, methyl tert-butyl ether, tetrahydrofuran, dioxane and the like; dimethyl formamide, dimethyl sulfoxide; dimethyl acetamide; water; or mixtures thereof.

In one embodiment, the Z-isomer, the compound of formula IIa, or salt thereof is selectively separated from the E-isomer, the compound of formula IIb, or salt thereof by being soluble in acetone and the E-isomer, or salt thereof being insoluble and precipitated out in acetone.

In one embodiment, the Z-isomer, the compound of formula IIa, or salt thereof is selectively separated from the E-isomer, the compound of formula IIb, or salt thereof by being soluble in acetone-water mixture and the E-isomer, or salt thereof being insoluble and precipitated out in acetone-water mixture.

In one embodiment, the sodium salt of Z-isomer, the compound of formula IIa, is selectively separated from the sodium salt of E-isomer, the compound of formula IIb, by being soluble in acetone and the salt of E-isomer being insoluble and precipitated out in acetone.

In one embodiment, the sodium salt of Z-isomer, the compound of formula IIa, is selectively separated from the sodium salt of E-isomer, the compound of formula IIb, by being soluble in acetone-water mixture and the salt of E-isomer being insoluble and precipitated out in acetone-water mixture.

In one embodiment, the Z-isomer, the compound of formula IIa, or salt thereof is selectively separated from the E-isomer, the compound of formula IIb, or salt thereof from the reaction mixture obtained in step (i) by a process comprising:
(p) removing the solvent of step (i); and
(q) optionally, adding a second solvent to step (p).

In one embodiment, (p) of the above process involves partial or complete removal of the solvent.

In one embodiment, the removal of solvent is carried out by methods selected from the group consisting of filtration, distillation, evaporation, centrifugation, spray drying and freeze drying.

In one embodiment, (q) of the above process involves optional addition of a second solvent to the step (p).

The addition of a second solvent is carried out, optionally if the solvent is completely removed in the above step (p).

In one embodiment, the Z-isomer, the compound of formula IIa, or salt thereof is selectively separated from the E-isomer, the compound of formula IIb, or salt thereof by completely removing the solvent of step (i) and addition of a second solvent to obtain a slurry.

In one embodiment, in the obtained slurry the E-isomer, the compound of formula IIb, or salt thereof remains insoluble and the Z-isomer, the compound of formula IIa, or salt thereof remains in solution.

In one embodiment, in the obtained slurry the Z-isomer, the compound of formula IIa, or salt thereof remains insoluble and the E-isomer, the compound of formula IIb, or salt thereof remains in solution.

In one embodiment, the E-isomer, the compound of formula IIb, or salt thereof is selectively separated from the above slurry by methods known in the art such as filtration, centrifugation and the like.

In one embodiment, the Z-isomer, the compound of formula IIa, or salt thereof is selectively separated from the above slurry by methods known in the art such as filtration, centrifugation and the like.

The second solvent includes but is not limited to ketones such as acetone, ethyl methyl ketone, methyl isobutyl ketone and the like; haloalkanes such as dichloromethane, chloroform, ethylene dichloride, and the like; alcohols such as methanol, ethanol, 1-propanol, 2-propanol, 1-butanol, 2-butanol, 1-pentanol, 1-octanol and the like; esters such as methyl acetate, ethyl acetate, n-propyl acetate, isopropyl acetate, tert-butyl acetate and the like; hydrocarbons such as toluene, xylene, chlorobenzene, heptane, hexane and the like; ethers such as diethyl ether, diisopropyl ether, methyl tert-butyl ether, tetrahydrofuran, dioxane and the like; dimethyl formamide, dimethyl sulfoxide; dimethyl acetamide; water; or mixtures thereof.

In (iii) of the above process, the separated Z-isomer, the compound of formula IIa, or salt thereof and the E-isomer, the compound of formula IIb, or salt thereof are optionally treated with an acid.

In one embodiment, the salt of the Z-isomer is optionally treated with an acid.

In one embodiment, the salt of the E-isomer is optionally treated with an acid.

A suitable acid includes, but is not limited to hydrochloric acid, hydrobromic acid, sulfuric acid, phosphoric acid, trifluoroacetic acid. Preferably, the acid selected is hydrochloric acid.

In one embodiment, the sodium salt of the Z-isomer is optionally treated with hydrochloric acid.

In one embodiment, the sodium salt of the E-isomer is optionally treated with hydrochloric acid.

In (c) of the process for the preparation of ospemifene, a compound of formula I, the undesired E-isomer, the compound of formula IIb, or a salt thereof is recycled to generate an isomeric mixture of Z,E-4-(4-hydroxy-1,2-diphenylbut-1-enyl)phenol, the process comprising:
(i) providing a solution of the E-isomer, the compound of formula IIb, or a salt thereof, in a solvent;
(ii) stirring and/or heating the solution obtained in step (i) to generate an isomeric mixture of Z,E-4-(4-hydroxy-1,2-diphenylbut-1-enyl)phenol; and
(iii) isolating the isomeric mixture of Z,E-4-(4-hydroxy-1,2-diphenylbut-1-enyl)phenol.

In (i) of the above process, the E-isomer, the compound of formula IIb, or a salt thereof, is dissolved in a solvent to provide a solution.

A suitable solvent includes but is not limited to esters such as methyl acetate, ethyl acetate, n-propyl acetate, tert-butyl acetate and the like; hydrocarbons such as toluene, xylene, chlorobenzene, heptane, hexane and the like; ethers such as diethyl ether, diisopropyl ether, methyl tert-butyl ether, tetrahydrofuran, dioxane and the like; ketones such as acetone, ethyl methyl ketone, methyl isobutyl ketone and the like; alcohols such as methanol, ethanol, 1-propanol, 2-propanol, 1-butanol, 2-butanol, 1-pentanol, 1-octanol and the like; haloalkanes such as dichloromethane, chloroform, ethylene dichloride, and the like; dimethyl formamide, dimethyl sulfoxide; dimethyl acetamide; water; or mixtures thereof. Preferably, the solvent selected is ethyl acetate.

In (ii) of the above process, the solution obtained in step (i) is stirred and/or heated to generate an isomeric mixture of Z,E-4-(4-hydroxy-1,2-diphenylbut-1-enyl)phenol.

The step (ii) may be carried out at a temperature in the range of about 10° C. to about 150° C.

In one embodiment, the solution obtained in step (i) is stirred and/or heated at a temperature in the range of about 10° C. to about 150° C. to generate an isomeric mixture of Z,E-4-(4-hydroxy-1,2-diphenylbut-1-enyl)phenol.

In one embodiment, the solution obtained in step (i) is stirred at a temperature in the range of about 10° C. to about 150° C. to generate an isomeric mixture of Z,E-4-(4-hydroxy-1,2-diphenylbut-1-enyl)phenol. Preferably, the stirring is carried out at a temperature in the range of about 40° C. to about 80° C.

In one embodiment, the solution obtained in step (i) is heated at a temperature in the range of about 40° C. to about 150° C. to generate an isomeric mixture of Z,E-4-(4-hydroxy-1,2-diphenylbut-1-enyl)phenol. Preferably, the temperature selected is in the range of about 45° C. to about 90° C.

In one embodiment, the solution of the E-isomer, the compound of formula IIb, or a salt thereof in ethyl acetate is stirred and/or heated at a temperature in the range of about 10° C. to about 150° C. to generate an isomeric mixture of Z,E-4-(4-hydroxy-1,2-diphenylbut-1-enyl)phenol.

The step (ii) is carried out till the content of the Z-isomer, the compound of formula IIa, is not less than 48% in the isomeric mixture of Z,E-4-(4-hydroxy-1,2-diphenylbut-1-enyl)phenol.

In one embodiment, the solution obtained in step (i) is stirred and/or heated at a temperature in the range of about 10° C. to about 150° C. till the content of the Z-isomer, the compound of formula IIa, is not less than 48% in the isomeric mixture of Z,E-4-(4-hydroxy-1,2-diphenylbut-1-enyl)phenol.

In one embodiment, the solution of the E-isomer, the compound of formula IIb, or a salt thereof in ethyl acetate is stirred and/or heated at a temperature in the range of about 10° C. to about 150° C. till the content of the Z-isomer, the compound of formula IIa, is not less than 48% in the isomeric mixture of Z,E-4-(4-hydroxy-1,2-diphenylbut-1-enyl)phenol.

In (iii) of the above process, the isomeric mixture of Z,E-4-(4-hydroxy-1,2-diphenylbut-1-enyl)phenol is isolated by any method known in the art. The method, may involve any of techniques, known in the art, including concentration of solvent, filtration by gravity or by suction, centrifugation, and the like.

In (d) of the process for the preparation of ospemifene, a compound of formula I, the steps of isomeric separation of Z- and E-isomers of 4-(4-hydroxy-1,2-diphenylbut-1-enyl)phenol and recycling of E-isomer, the compound of formula IIb, to give isomeric mixture of Z,E-4-(4-hydroxy-1,2-diphenylbut-1-enyl)phenol are optionally repeated to increase the productivity of Z-isomer, the compound of formula IIa.

In (e) of the process for the preparation of ospemifene, the compound of formula I, the Z-isomer, the compound of formula IIa, or a salt thereof is converted to ospemifene, the process comprising:

(i) reacting the Z-isomer, the compound of formula IIa, or a salt thereof with a compound of formula III,

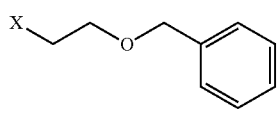

III wherein X is selected from the group consisting of Cl, Br, I, to form a compound of formula IV;

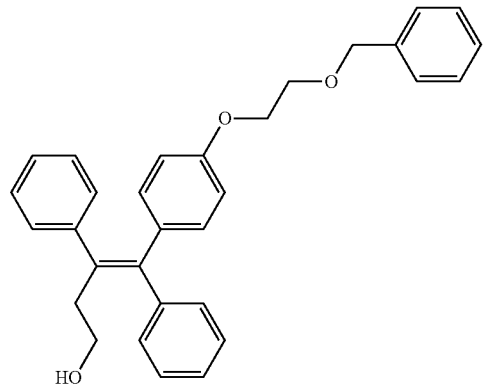

IV (ii) converting the compound of formula IV to a compound of formula V;

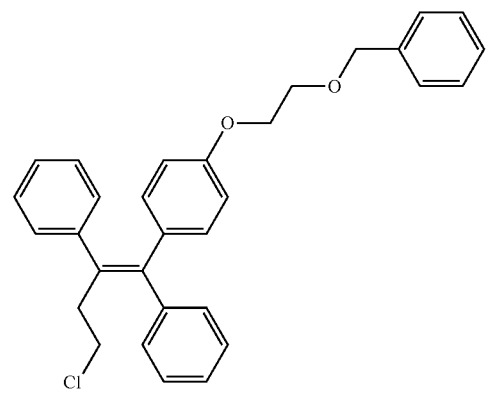

V (iii) deprotecting the compound of formula V to ospemifene.

In (i) of the above process, the Z-isomer, the compound of formula IIa, or a salt thereof is reacted with a compound of formula III.

The reaction may be carried out in the presence of a suitable base. The suitable base includes, but is not limited to alkali metal hydroxides such as lithium hydroxide, sodium hydroxide, potassium hydroxide; alkaline earth metal hydroxides; alkali metal hydrides such as sodium hydride, potassium hydride; alkali metal alcoholates such as lithium methoxide, sodium methoxide, potassium methoxide, rubidium methoxide, caesium methoxide, lithium ethoxide, sodium ethoxide, potassium ethoxide, sodium pentoxide, lithium tert-butoxide, sodium tert-butoxide, potassium tert-butoxide; alkaline earth metal alcoholates such as calcium ethoxide, magnesium iso-propoxide; alkyl lithium such as n-butyl lithium. Preferably the base selected is sodium hydroxide.

The reaction may be carried out in the presence of a suitable solvent. The suitable solvent includes, but is not limited to esters such as methyl acetate, ethyl acetate, n-propyl acetate, tert-butyl acetate and the like; hydrocarbons such as toluene, xylene and the like; ethers such as diethyl ether, diisopropyl ether, methyl tert-butyl ether, tetrahydrofuran, dioxane and the like; ketones such as acetone, ethyl methyl ketone, methyl isobutyl ketone and the like; alcohols such as methanol, ethanol, 1-propanol, 2-propanol, 1-butanol, 2-butanol, 1-pentanol, 1-octanol and the like; haloalkanes such as dichloromethane, chloroform, ethylene dichloride, and the like; dimethyl formamide, dimethyl sulfoxide; dimethyl acetamide; water or mixtures thereof. Preferably the solvent selected is toluene-water mixture.

The reaction may be carried out at a temperature in the range of about 30° C. to about the reflux temperature of the solvent. The reaction is carried out for a period of about 2 hours to about 15 hours. Preferably the reaction is carried out at a temperature of about 90° C. to about 105° C. for a period of about 6 hours to about 12 hours.

In (ii) of the above process, the compound of formula IV is converted to give a compound of formula V.

The reaction may be carried out in the presence of triphenylphosphine in carbon tetrachloride, triphenylphosphine-trichloroacetamide, cyanuric chloride, POCl₃, SOCl₂, oxalyl chloride in dimethyl formamide, N-chlorosuccinamide-triphenylphosphine.

In one embodiment, the compound of formula IV is converted to the compound of formula V using oxalyl chloride and dimethyl formamide.

The reaction may be carried out at a temperature in the range of about 30° C. to about the reflux temperature of the solvent. The reaction is carried out for a period of about 2 hours to about 10 hours. Preferably the reaction is carried out at a temperature of about 45° C. to about 85° C. for a period of about 2 hours to about 8 hours.

In (iii) of the above process, the compound of formula V is deprotected to give ospemifene.

The deprotection reaction may be carried out via hydrogenation reaction using hydrogen in the presence of a metal catalyst. A suitable metal catalyst includes but is not limited to palladium catalyst selected from palladium hydroxide on carbon, palladium on carbon; platinum, Raney nickel.

The reaction may be optionally carried out in the presence of an acid selected from hydrochloric acid, hydrobromic acid, sulfuric acid, phosphoric acid, trifluoroacetic acid. Preferably, the acid selected is hydrochloric acid.

In one embodiment, the compound of formula V is deprotected by hydrogenation using palladium catalyst in the presence of an acid to give ospemifene.

The present invention provides a process for the preparation of ospemifene, a compound of formula I,

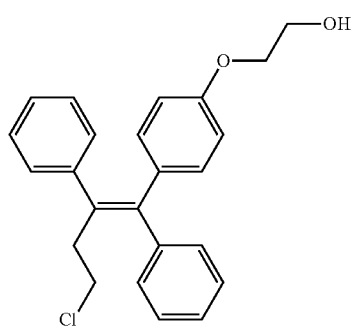

and pharmaceutically acceptable salts thereof, the process comprising:
(a) providing an isomeric mixture of Z,E-4-(4-hydroxy-1,2-diphenylbut-1-enyl)phenol;
(b) separating the desired Z-isomer, a compound of formula IIa, or a salt thereof and the undesired E-isomer, a compound of formula IIb, or a salt thereof from the isomeric mixture of Z,E-4-(4-hydroxy-1,2-diphenylbut-1-enyl)phenol;

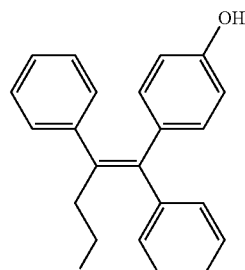

IIa

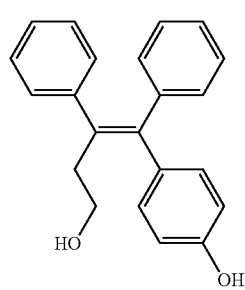

IIb (c) optionally, recycling the undesired E-isomer, the compound of formula IIb, or a salt thereof to generate an isomeric mixture of Z,E-4-(4-hydroxy-1,2-diphenylbut-1-enyl)phenol;
(d) optionally, repeating steps (b) and (c);
(e) reacting the Z-isomer, the compound of formula IIa, or a salt thereof with a compound of formula III,

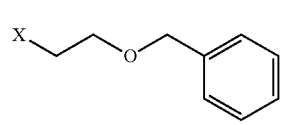

III wherein X is selected from the group consisting of Cl, Br, I, to form a compound of formula IV;

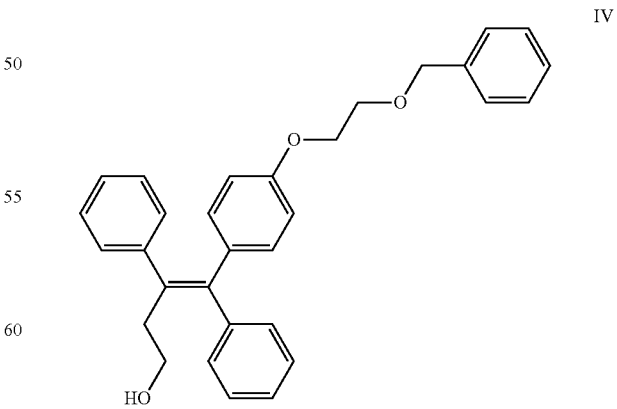

IV (f) converting the compound of formula IV to a compound of formula V using oxalyl chloride and dimethyl formamide; and

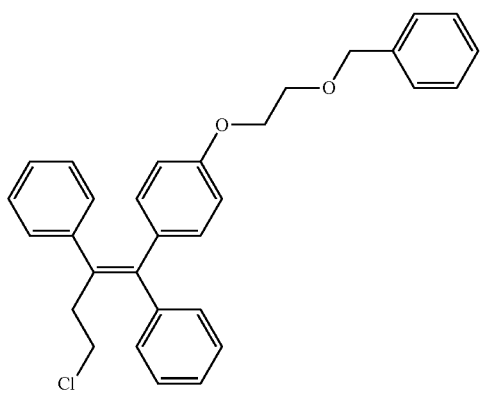

(g) deprotecting the compound of formula V to ospemifene.

The process steps (a), (b), (c), (d), (e), (f) and (g) are as discussed supra.

The present invention provides a process for the preparation of ospemifene, a compound of formula I,

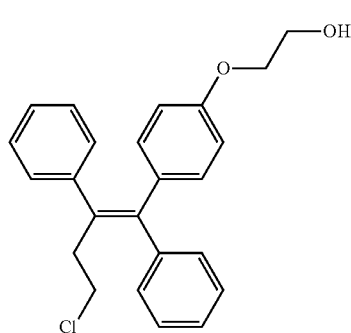

and pharmaceutically acceptable salts thereof, the process comprising:
(a) providing an isomeric mixture of Z,E-4-(4-hydroxy-1,2-diphenylbut-1-enyl)phenol;
(b) separating the desired Z-isomer, a compound of formula IIa, or a salt thereof and the undesired E-isomer, a compound of formula IIb, or a salt thereof from the isomeric mixture of Z,E-4-(4-hydroxy-1,2-diphenylbut-1-enyl)phenol;

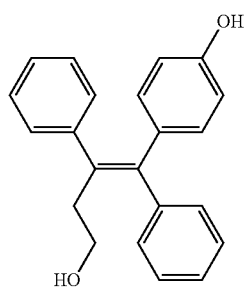

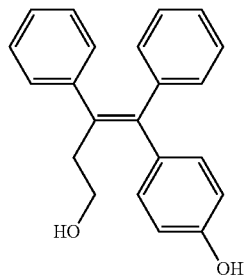

(c) recycling the undesired E-isomer, the compound of formula IIb, or a salt thereof to generate an isomeric mixture of Z,E-4-(4-hydroxy-1,2-diphenylbut-1-enyl)phenol;
(d) repeating steps (b) and (c); and
(e) converting the Z-isomer of 4-(4-hydroxy-1,2-diphenylbut-1-enyl)phenol, the compound of formula IIa, or a salt thereof obtained in step (b) to ospemifene.

The process steps (a), (b), (c), (d) and (e) are as discussed supra.

The present invention provides a process for the preparation of ospemifene, a compound of formula I,

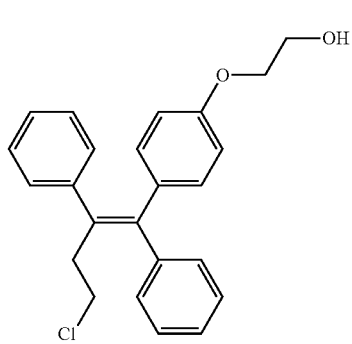

the process comprising:
(a) subjecting E-4-(4-hydroxy-1,2-diphenylbut-1-enyl)phenol, a compound of formula IIb, or a salt thereof to recycling to generate an isomeric mixture of Z,E-4-(4-hydroxy-1,2-diphenylbut-1-enyl)phenol;

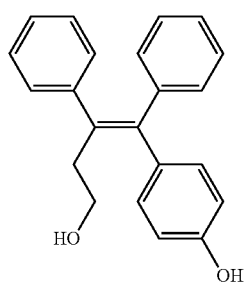

(b) separating the desired Z-isomer, a compound of formula IIa, or a salt thereof and the undesired E-isomer, the compound of formula IIb, or a salt thereof from the isomeric mixture of Z,E-4-(4-hydroxy-1,2-diphenylbut-1-enyl)phenol; and

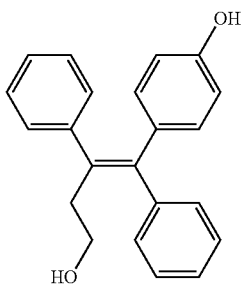

(c) converting the Z-isomer, the compound of formula IIa, or a salt thereof obtained in step (b) to ospemifene.

The process steps (a), (b) and (c) are as discussed supra.

The present invention provides a recycling process for the preparation of Z-4-(4-hydroxy-1,2-diphenylbut-1-enyl)phenol, a compound of formula IIa, or a salt thereof, the process comprising:
(a) providing a solution of the E-isomer of 4-(4-hydroxy-1,2-diphenylbut-1-enyl)phenol, a compound of formula IIb, or a salt thereof, in a solvent;
(b) stirring and/or heating the solution obtained in step (a) to generate an isomeric mixture of Z,E-4-(4-hydroxy-1,2-diphenylbut-1-enyl)phenol;
(c) isolating the isomeric mixture of Z,E-4-(4-hydroxy-1,2-diphenylbut-1-enyl)phenol;
(d) subjecting the isomeric mixture of Z,E-4-(4-hydroxy-1,2-diphenylbut-1-enyl)phenol to treatment with a base in a solvent to generate a reaction mixture;
(e) separating the desired Z-isomer, the compound of formula IIa, or a salt thereof and the undesired E-isomer, the compound of formula IIb, or a salt thereof from the reaction mixture obtained in step (d); and
(f) optionally, treating the separated Z-isomer, the compound of formula IIa, or a salt thereof and the E-isomer, the compound of formula IIb, or a salt thereof with an acid.

The process steps (a), (b), (c), (d), (e) and (f) are as discussed supra.

In one embodiment, the yield of ospemifene is at least 75% with respect to Z,E-4-(4-hydroxy-1,2-diphenylbut-1-enyl)phenol.

The present invention provides a process for purification of ospemifene comprising:
(a) providing a solution of ospemifene;
(b) precipitating out ospemifene from the solution obtained in step (a); and
(c) isolating the solid formed in step (b) to give pure ospemifene.

In (a) of the above process, ospemifene is dissolved in a solvent or a mixture of solvents to form a solution.

The suitable solvent includes but is not limited to esters such as methyl acetate, ethyl acetate, n-propyl acetate, isopropyl acetate, tert-butyl acetate and the like; hydrocarbons such as toluene, xylene, chlorobenzene, heptane, hexane and the like; ethers such as diethyl ether, diisopropyl ether, methyl tert-butyl ether, tetrahydrofuran, dioxane and the like; ketones such as acetone, ethyl methyl ketone, methyl isobutyl ketone and the like; alcohols such as methanol, ethanol, 1-propanol, 2-propanol, 1-butanol, 2-butanol, 1-pentanol, 1-octanol and the like; haloalkanes such as dichloromethane, chloroform, ethylene dichloride, and the like; acetonitrile, dimethyl formamide, dimethyl sulfoxide; dimethyl acetamide; water; or mixtures thereof. Preferably the solvent selected is methanol, ethanol, 2-propanol, acetonitrile, ethanol-water mixture, acetonitrile-water mixture.

Suitable temperature for dissolution of ospemifene may range from about room temperature to about the reflux temperature of the solvent. The stirring time may range from about 30 minutes to about 3 hours, or longer. The solution may be optionally treated with charcoal and filtered to get a particle-free solution.

In (b) of the above process, ospemifene is precipitated out from the solution obtained in the step (a).

In one embodiment, ospemifene is precipitated out by addition of an anti-solvent to the solution of the step (a).

The suitable anti-solvent includes but is not limited to ketones such as acetone, ethyl methyl ketone, methyl isobutyl ketone and the like; haloalkanes such as dichloromethane, chloroform, ethylene dichloride, and the like; alcohols such as methanol, ethanol, 1-propanol, 2-propanol, 1-butanol, 2-butanol, 1-pentanol, 1-octanol and the like; esters such as methyl acetate, ethyl acetate, n-propyl acetate, isopropyl acetate, tert-butyl acetate and the like; hydrocarbons such as toluene, xylene, chlorobenzene, heptane, hexane and the like; ethers such as diethyl ether, diisopropyl ether, methyl tert-butyl ether, tetrahydrofuran, dioxane and the like; acetonitrile, dimethyl formamide, dimethyl sulfoxide; dimethyl acetamide; water; or mixtures thereof.

Preferably the solvent selected is water.

In one embodiment, ospemifene is dissolved in ethanol at about reflux temperature to form a solution and ospemifene is precipitated out by addition of water.

In one embodiment, ospemifene is precipitated out by cooling the solution of the step (a) to about room temperature or below with or without stirring. The time required for precipitation of ospemifene may range from about 30 minutes to about 15 hours, or longer.

In (c) of the above process, the solid formed in (b) is isolated from the solution to give pure ospemifene by any method known in the art. The method, may involve any of techniques, known in the art, including filtration by gravity or by suction, centrifugation, and the like.

In one embodiment, the present invention provides ospemifene obtained by above process, having a particle size distribution wherein the $D_{50}$ particle size is in the range of about 15 microns to about 75 microns and the $D_{90}$ particle size is in the range of about 50 microns to about 150 microns.

In one embodiment, the present invention provides ospemifene obtained by above process, having a $D_{50}$ particle size of less than about 15 microns and $D_{90}$ particle size in the range of about 50 microns to about 150 microns.

In one embodiment, the present invention provides ospemifene obtained by above process, having a $D_{50}$ particle size in the range of about 15 microns to about 75 microns and $D_{90}$ particle size of less than about 50 microns.

As used herein the term "particle size distribution" means the cumulative volume size distribution of equivalent spherical diameters. $D_{50}$ refers to the value of the particle diameter at 50% in the cumulative distribution. $D_{90}$ refers to the value of the particle diameter at 90% in the cumulative distribution.

The present invention provides a process for the preparation of ospemifene, having a particle size distribution wherein the $D_{50}$ particle size is in the range of about 15 microns to about 75 microns and the $D_{90}$ particle size is in the range of 50 microns to about 150 microns, the process comprising:

(a) providing a solution of ospemifene in a solvent selected from alcohols, nitriles, water, or mixture thereof;
(b) precipitating out ospemifene from the solution obtained in step (a); and
(c) isolating the solid formed in step (b) to give ospemifene, having a $D_{50}$ particle size in the range of about 15 microns to about 75 microns and $D_{90}$ particle size in the range of 50 microns to about 150 microns.

In (a) of the above process, ospemifene is dissolved in a solvent selected from alcohols such as methanol, ethanol, 1-propanol, 2-propanol, 1-butanol, 2-butanol, 1-pentanol, 1-octanol and the like; nitriles such as acetonitrile; water, or mixture thereof.

The reaction may be carried out at a temperature in the range of about room temperature to about 150° C. The stirring time may range from about 30 minutes to about 3 hours, or longer.

In one embodiment, the step (a) is carried out at a temperature in the range of about 40° C. to about 120° C.

In (b) of the above process, ospemifene is precipitated out from the solution obtained in the step (a).

The step (b) may be carried out at a temperature in the range of about −5° C. to 30° C.

In one embodiment, ospemifene is precipitated out by cooling the solution of step (a) to about room temperature or below without stirring. The time required for precipitation of ospemifene may range from about 30 minutes to about 24 hours, or longer.

In one embodiment, ospemifene is dissolved in ethanol-water mixture at about 75° C. to about 80° C. to form a solution and ospemifene is precipitated out by cooling the solution to about room temperature or below without stirring.

In (c) of the above process, the solid formed in step (b) is isolated from the solution to give ospemifene having a $D_{50}$ particle size in the range of about 15 microns to about 75 microns and $D_{90}$ particle size in the range of 50 microns to about 150 microns by any method known in the art. The method, may involve any of techniques, known in the art, including filtration by gravity or by suction, centrifugation, and the like.

In one embodiment, the present invention provides a process for ospemifene, having a particle size distribution wherein the $D_{50}$ particle size is in the range of about 15 microns to about 75 microns and the $D_{90}$ particle size is in the range of about 50 microns to about 150 microns, the process comprising:
(a) providing a solution of ospemifene in a solvent selected from alcohols, nitriles at about 40° C. to about 120° C.;
(b) optionally, adding water to the solution obtained in step (a) at about 40° C. to about 120° C.;
(c) precipitating out ospemifene by cooling the solution obtained in step (b) to about −5° C. to about 30° C. without stirring; and
(d) isolating the solid formed in step (c) to give ospemifene, having a $D_{50}$ particle size in the range of about 15 microns to about 75 microns and $D_{90}$ particle size in the range of 50 microns to about 150 microns.

In one embodiment, ospemifene is dissolved in methanol at about 50° C. to about 55° C. to give a solution and ospemifene is precipitated out by cooling the solution of ospemifene to about room temperature without stirring to give ospemifene having a $D_{50}$ particle size in the range of about 15 microns to about 75 microns and $D_{90}$ particle size in the range of 50 microns to about 150 microns.

In one embodiment, ospemifene is dissolved in 2-propanol at about 50° C. to about 55° C. to give a solution and ospemifene is precipitated out by cooling the solution of ospemifene to about room temperature without stirring to give ospemifene having a $D_{50}$ particle size in the range of about 15 microns to about 75 microns and $D_{90}$ particle size in the range of 50 microns to about 150 microns.

In one embodiment, ospemifene is dissolved in acetonitrile at about 50° C. to about 55° C. to give a solution and ospemifene is precipitated out by cooling the solution of ospemifene to about room temperature without stirring to give ospemifene having a $D_{50}$ particle size in the range of about 15 microns to about 75 microns and $D_{90}$ particle size in the range of 50 microns to about 150 microns.

In one embodiment, the present invention provides a process for ospemifene, having $D_{50}$ particle size in the range of about 15 microns to about 75 microns and $D_{90}$ particle size in the range of about 50 microns to about 150 microns, the process comprising:
(a) providing a solution of ospemifene in ethanol at about 75° C. to about 80° C.;
(b) adding water to the solution obtained in step (a) at about 75° C. to about 80° C.;
(c) precipitating out ospemifene by cooling the solution obtained in step (b) to about room temperature without stirring; and
(d) isolating the solid formed in step (c).

In one embodiment, the present invention provides ospemifene obtained by above process, having a $D_{50}$ particle size in the range of about 20 microns to about 70 microns and $D_{90}$ particle size in the range of about 55 microns to about 120 microns.

In one embodiment, the present invention provides ospemifene obtained by above process, having a $D_{50}$ particle size of about 22 microns and $D_{90}$ particle size of about 69 microns.

In one embodiment, the present invention provides ospemifene obtained by above process, having a $D_{50}$ particle size of about 36 microns and $D_{90}$ particle size of about 84 microns.

In one embodiment, the present invention provides ospemifene obtained by above process, having a $D_{50}$ particle size of about 31 microns and $D_{90}$ particle size of about 102 microns.

The present invention provides a process for ospemifene, having a particle size distribution wherein the $D_{50}$ particle size is less than about 15 microns and the $D_{90}$ particle size is less than about 50 microns, the process comprising:
(a) providing a solution of ospemifene in a solvent selected from alcohols, nitriles, water, or mixture thereof;
(b) precipitating out ospemifene by cooling the solution obtained in step (a) to about room temperature or below with stirring; and
(c) isolating the solid formed in step (b) to give ospemifene, having a $D_{50}$ particle size less than about 15 microns and $D_{90}$ particle size less than about 50 microns.

In one embodiment, the present invention provides a process for ospemifene, having a particle size distribution wherein the $D_{50}$ particle size is less than about 15 microns and the $D_{90}$ particle size is less than about 50 microns, the process comprising:
(a) providing a solution of ospemifene in ethanol at about 75° C. to about 80° C.;
(b) adding water to the solution obtained in step (a) at about 75° C. to about 80° C.;
(c) precipitating out ospemifene by cooling the solution obtained in step (b) to 10° C. to about 30° C. with stirring; and (d) isolating the solid formed in step (c) to give ospemifene having a $D_{50}$ particle size less than about 15 microns and $D_{90}$ particle size less than about 50 microns.

In one embodiment, the present invention provides ospemifene obtained by above process, having a $D_{50}$ particle size of about 7 microns and $D_{90}$ particle size of about 28 microns.

The methodology and protocols for particle size distribution of ospemifene by laser diffraction are described below:

Instrument: Malvern Mastersizer 2000
Sample Handling Unit: Hydro2000S (A)
Range: 0.02 μm to 2000 μm
Pump/Stirrer Speed: 1500 rpm
Dispersant: Water
Sample Preparation: Transfer about 50-100 mg of well mixed sample in a beaker. Add 30 ml of 0.5% w/v solution of Tween 80 in water and sonicate for 180 seconds with continuous stirring.
Obscuration: Between 10-20%

In one embodiment, the present invention provides ospemifene which is substantially free of E-isomer of ospemifene.

In the present application, the term "substantially free" means the E-isomer of ospemifene is less than 0.10% w/w with respect to ospemifene, as determined by high performance liquid chromatography (HPLC).

The present invention provides ospemifene wherein the E-isomer of ospemifene is present to an extent of less than 0.10% w/w relative to the amount of ospemifene, obtained by above process, as analyzed by chemical purity using high performance liquid chromatography (HPLC) with the conditions described below:

Reagents, Solvents and Standards: Water (Milli Q or equivalent), Acetonitrile (HPLC Grade), Methanol (HPLC Grade), Tetrahydrofuran (HPLC Grade), Ammonium dihydrogen phosphate (AR grade)

Chromatographic Conditions:
Apparatus: A High Performance Liquid Chromatograph equipped with quaternary gradient pumps, variable wavelength UV detector attached with data recorder and integrator software.
Column: Waters symmetry C8, 250×4.6 mm, 5μ
Column temperature: 25° C.
Mobile Phase:
Mobile Phase A=Buffer: Tetrahydrofuran, (95:05, v/v)
Buffer: 0.01M Ammonium dihydrogen phosphate in water.
Mobile Phase B=Acetonitrile: Methanol: Tetrahydrofuran, (85:10:05, v/v/v)

| Time (min.) | % Mobile Phase A | % Mobile Phase B |
|---|---|---|
| 0.01 | 50 | 50 |
| 30 | 30 | 70 |
| 70 | 30 | 70 |
| 75 | 50 | 50 |
| 80 | 50 | 50 |

Diluent: Water: Acetonitrile (20:80, v/v)
Flow Rate: 1.0 mL/minute
Detection: UV 225 nm
Injection Volume: 20 μL
The retention time of ospemifene is about 24.0 minutes under these conditions.
Relative retention time for E-isomer of ospemifene is about 0.95 with respect to ospemifene.

In one embodiment, the present invention provides ospemifene wherein the compound of formula X is less than 0.15% w/w with respect to ospemifene, as determined by high performance liquid chromatography (HPLC).

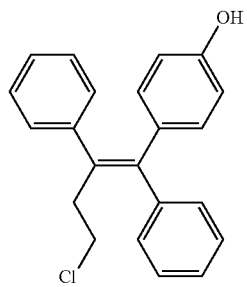

X

In one embodiment, the present invention provides ospemifene free of any of the below listed impurities—

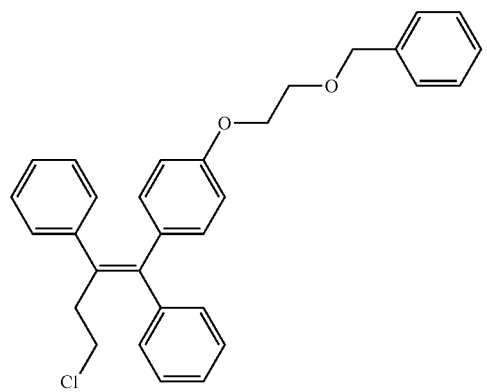

V

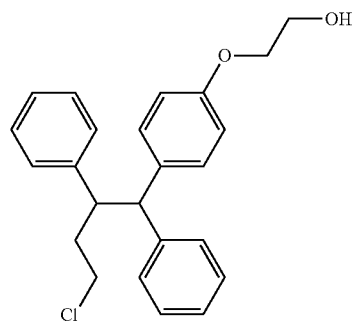

XI

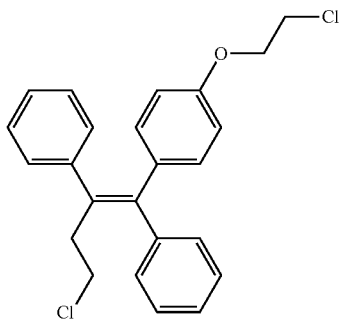

XII

-continued

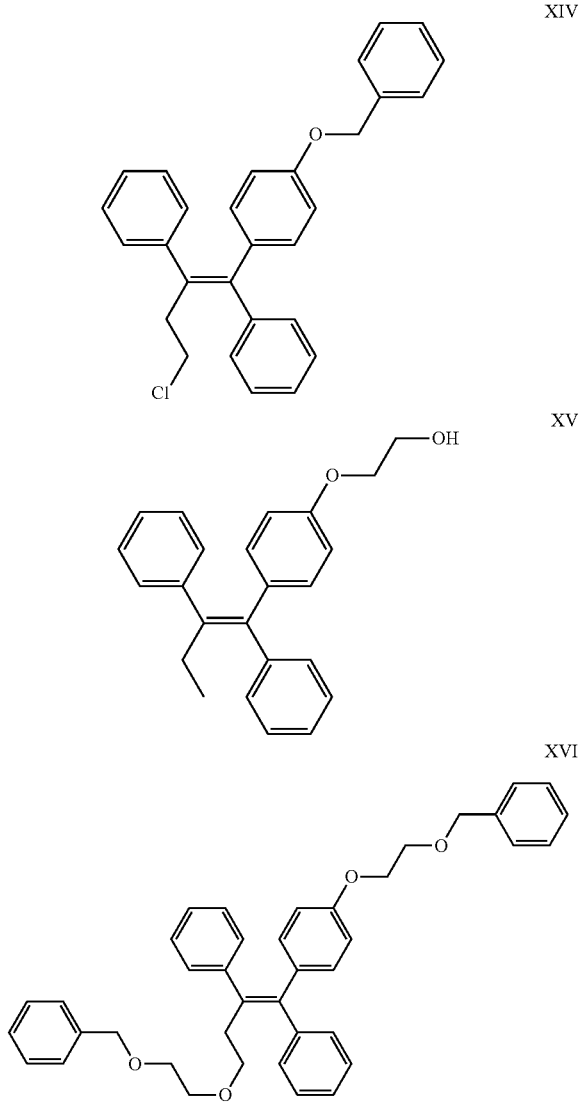

XIII

XIV

XV

XVI

In one embodiment, the present invention provides ospemifene characterized by DSC thermogram having an endothermic peak at about 119±2° C.

In one embodiment, the present invention provides ospemifene characterized by DSC thermogram having an endothermic peak at about 121±2° C.

In one embodiment, the present invention provides ospemifene characterized by an X-ray powder diffraction pattern, which is substantially in accordance with FIG. 1.

The X-ray powder diffraction profile was obtained using an X-ray Diffractometer (Philips X'Pert Pro, PANalytical). The measurements were carried out with a Pre FIX module programmable divergence slit and anti-scatter Slit (Offset 0.00°); target, Cu; filter, Ni; detector, X'Celerator; Scanning Mode; Active length (2Theta)=2.122°; generator 45 KV; tube current 40mAmp. The samples were scanned in the full 2θrange of 2–50° with a "time-per-step" optimized to 50 sec.

The examples that follow are provided to enable one skilled in the art to practice the invention and are merely illustrative of the invention. The examples should not be read as limiting the scope of the invention.

EXAMPLES

Example 1 Preparation of 4-[(tetrahydropyran-2-yl) oxy]-1,2-diphenylbutan-1-one

To a mixture of deoxybenzoin (15 g) and 2-(2-bromoethoxy)tetrahydro-2H-pyran (12.3 g) was added benzyltriethylammonium chloride (0.5 g) and the reaction mixture was heated to about 80° C. 48% Aqueous sodium hydroxide solution was then drop wise added to the reaction mixture under stirring at about 80° C. and the reaction mixture was stirred for about 15 h. The reaction mixture was then cooled to about room temperature and water and toluene were added to it under stirring. The reaction mixture was stirred for about 30 min and the two layers were separated. The aqueous layer was again extracted with toluene. The combined organic layer was washed with water, concentrated under vacuum to give an oily product. Yield: 24 g Example 2 Preparation of 4-[(tetrahydropyran-2-yl) oxy]-1,2-diphenyl-1-(4-methoxyphenyl)butan-1-ol A solution of p-bromophenol (8.47 g) in tetrahydrofuran (10 mL) was slowly added to a mixture of tetrahydrofuran (10 mL) and magnesium turnings (1.1 g) under nitrogen atmosphere at about reflux temperature and the reaction mixture was maintained for about 2 h. A mixture of 4-[(tetrahydropyran-2-yl)oxy]-1,2-diphenylbutan-1-one (10.7 g) and tetrahydrofuran (10 mL) was then added drop wise to the above reaction mixture and the reaction mixture was maintained at about the reflux temperature for about 2 h. The reaction mixture was concentrated under vacuum to give a residue. To the residue, ammonium chloride solution was added and the reaction mixture was extracted with ethyl acetate. The two layers were separated and the aqueous layer was again extracted with ethyl acetate. The combined organic layer was concentrated under vacuum and degassed to give a thick residue. Yield: 17 g Example 3 Preparation of 2-(4-methoxyphenyl)-2,3-diphenyltetrahydrofuran To a stirred mixture of 4-[(tetrahydropyran-2-yl)oxy]-1, 2-diphenyl-1-(4-methoxyphenyl)butan-1-ol (10.2 g) and methanol (28.5 mL) was added a mixture of concentrated sulphuric acid (2.38 g) and water (8.93 mL). The reaction mixture was heated to about 45° C. to about 50° C. under stirring for about 4 h. The reaction mixture was cooled to about room temperature and dilute sodium hydroxide solution was drop wise added to it to adjust the pH to about 5.5 to about 6.5. The reaction mixture was concentrated under vacuum to give a residue. Water and ethyl acetate were added to the residue and the reaction mixture was stirred for about 30 min. The two layers were separated and the aqueous layer was extracted with ethyl acetate. The combined organic layer was concentrated under vacuum and degassed to give oily residue which was purified by dissolving it in isopropyl alcohol at about reflux temperature followed by cooling to about below 10° C. The solid obtained was filtered and dried under vacuum. Yield: 3.8 g Example 4 Preparation of Z,E-4-(4-hydroxy-1,2-diphenylbut-1-enyl)phenol To a mixture of 2-(4-methoxyphenyl)-2,3-diphenyltetrahydrofuran (10.5 g) and acetic acid (15.8 mL) was added 35% HBr in acetic acid (15.8 mL) and the reaction mixture was heated to about 75° C. to about 80° C. and stirred for about 2 h. A second lot of 35% HBr in acetic acid was added at about room temperature and the reaction mixture was heated to about 75° C. to about 80° C. and stirred for about 4 h. The reaction mixture was concentrated under vacuum and degassed to give a thick oily residue which was dissolved in methanol and water. The pH of the reaction mixture was adjusted to about more than 12 by adding aqueous sodium hydroxide solution. The reaction mixture was heated to about 75° C. to about 80° C. and was maintained for about 5 h. The pH of the reaction mixture was adjusted to about 6.8 to about 7.2 by adding aqueous hydrochloric acid solution. The reaction mixture was extracted with water and ethyl acetate. The two layers were separated and the organic layer was treated with activated charcoal, filtered, concentrated under vacuum and degassed to give thick residue which was slurred in toluene and the solid obtained was filtered and dried under vacuum. Yield: 4.5 g Example 5 Preparation of sodium Z-4-(4-hydroxy-1,2-diphenylbut-1-enyl)phenolate A mixture of Z,E-4-(4-hydroxy-1,2-diphenylbut-1-enyl) phenol (4.4 g), sodium hydroxide (4.4 g) and water was stirred at about room temperature. The solid obtained was filtered and dried. The solid obtained was slurred in acetone at about 50° C. for about 2 h. The insoluble solid was filtered and washed with acetone. The insoluble solid obtained is the sodium salt of the E-isomer.

The filtrate containing the sodium salt of the desired Z-isomer was concentrated to give a residue and the obtained residue was slurred in methylene dichloride. The solid obtained was filtered, washed with methylene dichloride and dried under vacuum. The obtained solid is the sodium salt of the Z-isomer (2.2 g).

Example 6 Preparation of Z,E-4-(4-hydroxy-1,2-diphenylbut-1-enyl)phenol

To the mixture of sodium E-4-(4-hydroxy-1,2-diphenylbut-1-enyl)phenolate (2.9 g) prepared as in Example 5, water and ethyl acetate, was added 1:1 hydrochloric acid to adjust the pH to about 4.5 to about 5.5 and the mixture was stirred at about room temperature. The two layers were separated and the ethyl acetate layer was stirred at about 45° C. to about 50° C. till the Z-isomer is not less than 48% by HPLC analysis. The solvent was concentrated under vacuum and degassed to give a residue. The obtained residue was slurred in toluene and the solid obtained was filtered and dried under vacuum.

Example 7 Preparation of Z-4-[4-(2-benzyloxyethoxy)phenyl]-3,4-diphenylbut-3-en-1-ol To a stirred mixture of sodium Z-4-(4-hydroxy-1,2-diphenylbut-1-enyl)phenolate (2.1 g) prepared as in Example 5, tetrabutylammonium bromide (0.11 g) and toluene (27.3 mL), was added 48% aqueous sodium hydroxide solution followed by 2-bromoethoxymethylbenzene (0.8 g). The reaction mixture was maintained at about the reflux temperature for about 4 h. The reaction mixture was cooled to about room temperature and filtered. The filtrate was collected and the two layers were separated. The toluene layer was concentrated under vacuum and degassed to give pale yellow to brown color solid (1.44 g).

Example 8 Preparation of Z-1-[4-(2-benzyloxyethoxy)phenyl]-4-chloro-1,2-diphenylbut-1-ene To a stirred mixture of Z-4-[4-(2-benzyloxyethoxy)phenyl]-3,4-diphenylbut-3-en-1-ol (2.1 g) prepared as in Example 7, and acetonitrile (12.6 mL), was added triphenyl phosphine (3.1 g) and carbon tetrachloride (7.4 g). The reaction mixture was stirred at about 45° C. to about 50° C. for about 2 h. The reaction mixture was concentrated under vacuum to give a residue. To the residue was added methanol and water and the mixture was stirred well. The precipitated solid product was filtered and dried under vacuum. The crude product was purified by dissolving in isopropanol at about the reflux temperature followed by cooling the reaction mixture to about room temperature. The solid obtained was filtered, washed with isopropanol and dried under vacuum. Yield: 1.6 g Example 9 Preparation of Ospemifene To a solution of 7 g of Z-1-[4-(2-benzyloxyethoxy)phenyl]-4-chloro-1,2-diphenylbut-1-ene in methanol (80 mL) was added 5% palladium on carbon (1.1 g). The reaction mixture was hydrogenated under hydrogen pressure of about 4 kg/cm$^2$ to about 5 kg/cm$^2$. The reaction mixture was filtered under nitrogen gas atmosphere and washed with methanol. The filtrate was concentrated under vacuum to give a residue which was dissolved in ethanol at about reflux temperature, treated with Norrit charcoal and filtered. To the obtained filtrate was added DM water and the resultant mixture was cooled to about room temperature, and was stirred for about 1 h. The solid obtained was filtered, washed with premixed solution of ethanol and water and dried under vacuum. Yield: 4.34 g; Purity: 99.5%; E-isomer: 0.1%

Example 10

Ospemifene (4.27 g) was purified by dissolving in ethanol (20.5 mL) at about reflux temperature followed by addition of water (7.69 mL) under stirring. The precipitated solid was filtered, washed with premixed solution of ethanol and water and dried under vacuum. Yield: 3.75 g
Purity: 99.71%; E-isomer: Not detected
XRPD peaks of ospemifene:

| Pos. [°2Th.] | d-spacing [Å] | Rel. Int. [%] |
|---|---|---|
| 7.41 | 11.91 | 4.35 |
| 8.56 | 10.32 | 5.33 |
| 11.27 | 7.84 | 34.06 |

-continued

| Pos. [°2Th.] | d-spacing [Å] | Rel. Int. [%] |
|---|---|---|
| 12.75 | 6.93 | 5.01 |
| 15.32 | 5.78 | 14.56 |
| 16.33 | 5.42 | 1.25 |
| 16.97 | 5.22 | 4.28 |
| 17.40 | 5.09 | 9.58 |
| 18.49 | 4.79 | 22.30 |
| 19.43 | 4.56 | 10.35 |
| 19.80 | 4.48 | 1.99 |
| 21.21 | 4.18 | 40.48 |
| 22.01 | 4.03 | 10.41 |
| 22.43 | 3.96 | 14.88 |
| 22.78 | 3.90 | 27.86 |
| 23.14 | 3.84 | 14.16 |
| 23.62 | 3.76 | 100.00 |
| 25.46 | 3.49 | 5.77 |
| 25.83 | 3.44 | 5.66 |
| 26.10 | 3.41 | 5.28 |
| 26.51 | 3.36 | 16.69 |
| 27.86 | 3.20 | 7.44 |
| 28.76 | 3.10 | 2.37 |
| 29.11 | 3.06 | 4.44 |
| 29.76 | 3.00 | 15.78 |
| 30.67 | 2.91 | 5.55 |
| 31.52 | 2.83 | 1.43 |
| 32.14 | 2.78 | 1.81 |
| 32.65 | 2.74 | 0.96 |
| 33.28 | 2.69 | 3.17 |
| 33.97 | 2.63 | 0.89 |
| 34.89 | 2.57 | 2.31 |
| 35.38 | 2.53 | 3.30 |

Example 11 Preparation of Ospemifene

To a solution of 10 g of Z-1-[4-(2-benzyloxyethoxy)phenyl]-4-chloro-1,2-diphenylbut-1-ene in methanol (50 mL) was added 10% palladium on carbon (1 g). The reaction mixture was hydrogenated under hydrogen pressure of about 3 kg/cm$^2$ to about 4 kg/cm$^2$. The reaction mixture was filtered under nitrogen gas atmosphere and washed with methanol. The filtrate was concentrated under vacuum to give a residue which was dissolved in a premixed solution of acetonitrile and water. The reaction mixture was heated to about 75° C. to about 80° C., maintained for about 30 min and then cooled to about room temperature to give a solid which was filtered. To the obtained solid was added a premixed solution of ethanol and water. The reaction mixture was heated to about 75° C. to about 80° C., maintained for about 30 min and then cooled to about room temperature to give a solid which was filtered, washed with premixed solution of ethanol and water and dried under vacuum.

Example 12

A mixture of ospemifene (1 g) and methanol (8 mL) was heated to about 50° C. to about 55° C. to get a clear solution. The solution was gradually cooled to about room temperature without stirring and maintained for about 12 h without stirring. The solid obtained was filtered and dried under vacuum. Yield: 0.7 g $D_{10}$: 5 µm; $D_{50}$: 22 µm; $D_{90}$: 68 µm Example 13

A mixture of ospemifene (1 g) and isopropanol (5 mL) was heated to about 50° C. to about 55° C. to get a clear solution. The solution was gradually cooled to about room temperature without stirring and maintained for about 12 h without stirring. The solid obtained was filtered and dried under vacuum. Yield: 0.75 g $D_{10}$: 7 µm; $D_{50}$: 21 µm; $D_{90}$: 56 µm Example 14

A mixture of ospemifene (1 g) and acetonitrile (8 mL) was heated to about 50° C. to about 55° C. to get a clear solution. The solution was gradually cooled to about room temperature without stirring and maintained for about 12 h without stirring. The solid obtained was filtered and dried under vacuum. Yield: 0.8 g $D_{10}$: 8 µm; $D_{50}$: 36 µm; $D_{90}$: 84 µm Example 15

A mixture of ospemifene (2 g) and methanol (30 mL) was heated to about 50° C. to about 55° C. to get a clear solution. The solvent was distilled out under vacuum at about 50° C. The solid obtained was degassed under vacuum at about 50° C. for about 4 h. Yield: 1.8 g $D_{10}$: 5 µm; $D_{50}$: 21 µm; $D_{90}$: 49 µm Example 16 Preparation of Z-4-[4-(2-benzyloxyethoxy)phenyl]-3,4-diphenylbut-3-en-1-ol A mixture of sodium Z,E-4-(4-hydroxy-1,2-diphenylbut-1-enyl)phenolate (10 g), acetone (135 mL) and water (15 mL) was stirred at about 50° C. to about 55° C. for about 2 h. The hot reaction mixture was filtered and washed with acetone. The insoluble solid obtained is the undesired E-isomer. The filtrate containing the desired Z-isomer was concentrated under vacuum and stripped out with toluene to give a residue and the obtained residue was slurred in toluene at about below 50° C. The solid obtained was filtered, washed with toluene and dried under vacuum. Yield: 4 g To a stirred mixture of above obtained solid in toluene (60 mL) was added sodium hydroxide solution at about room temperature followed by tetrabutylammonium bromide (0.2 g) and 2-bromoethoxymethylbenzene (2.6 g). The reaction mixture was stirred for about 8 h at about 90° C. to about 95° C. The reaction mixture was cooled to about room temperature, stirred for about 3 h and filtered. The two layers of the filtrate were separated and the organic layer was washed with brine solution and concentrated to give a residue which was slurred in n-heptane at about 60° to about 65°. The reaction mixture was cooled to about room temperature, filtered and washed with n-heptane. The solid obtained was purified in isopropyl alcohol. Yield: 3.4 g Example 17 Preparation of Z-1-[4-(2-benzyloxyethoxy)phenyl]-4-chloro-1,2-diphenylbut-1-ene To a stirred mixture of oxalyl chloride (2.5 g) in acetonitrile (30 mL) cooled to about 0° C. to about 5° C., was added dimethyl formamide (1.6 g). The reaction mixture was maintained for about 30 min and Z-4-[4-(2-benzyloxyethoxy)phenyl]-3,4-diphenylbut-3-en-1-ol (5 g) prepared as in Example 16, was added to it. The reaction mixture was heated to about 75° C. to about 80° C. for about 6 h to about 7 h. The reaction mixture was concentrated under vacuum to give a residue. To the residue was added methanol and water and the mixture was stirred for about 2 h. The solid obtained was filtered, dried under vacuum and purified in isopropyl alcohol. Yield: 4.5 g

Example 18 Preparation of Ospemifene

To a solution of 10 g of Z-1-[4-(2-benzyloxyethoxy)phenyl]-4-chloro-1,2-diphenylbut-1-ene in methanol (300 mL) was added 20% palladium hydroxide on carbon (0.6 g) and 3.4 g of concentrated hydrochloric acid under nitrogen gas atmosphere. The reaction mixture was hydrogenated under hydrogen pressure of about 1 kg/cm$^2$ to about 1.5 kg/cm$^2$. The reaction mixture was filtered over hyflo bed under nitrogen gas atmosphere and washed with methanol. The filtrate was concentrated under vacuum to give a residue which was purified in isopropyl alcohol and n-heptane and further purified in ethanol and water. Yield: 7 g

Example 19

Ospemifene (5.8 g) was dissolved in a mixture of ethanol (24.5 mL) and water (10.5 mL) at about 75° C. The reaction mixture was maintained for about 40 min at about 75° C. and was cooled to about room temperature and further cooled to about 15° C. and stirred for about 2 h. The solid obtained was filtered, washed with ethanol-water (70:30) mixture and dried in vacuum at about 55° C. for about 10 h. Yield: 3.4 g $D_{10}$: 2.4 μm; $D_{50}$: 7.2 μm; $D_{90}$: 27.8 μm

Example 20

Ospemifene (3 g) was dissolved in ethanol (14.7 mL) at about 75° C. and the clear solution was filtered through hyflo bed. Water (6.3 mL) was added to the clear filtrate and the reaction mixture was stirred at about 75° C. for about 30 min to about 40 min. The reaction mixture was cooled to about room temperature without stirring over a period of about 12 h. The solid obtained was filtered, washed with ethanol-water mixture and dried in vacuum at about 55° C. for about 12 h. Yield: 2.76 g $D_{10}$: 7.9 μm; $D_{50}$: 30.1 μm; $D_{90}$: 101.3 μm

Example 21 Preparation of Z,E-4-(4-hydroxy-1,2-diphenylbut-1-enyl)phenol

The recovered undesired E-isomer (29.7 g) prepared as in Example 16, was treated with water (297 mL) and hydrochloric acid (29.7 mL) at about room temperature for about 40 min. The solid obtained was filtered and washed with water. The wet solid was dissolved in ethyl acetate (150 mL) and the two layers were separated. The organic layer was refluxed for about 12 h till the Z-isomer is not less than 48% by HPLC analysis. The solvent was concentrated under vacuum and the residue was slurred in toluene at about 60° C. for about 1 h. The solid obtained was filtered, washed with toluene and dried under vacuum at about 60° C. for about 12 h. Yield: 18 g

The invention claimed is:

1. A process for the preparation of ospemifene, a compound of formula I,

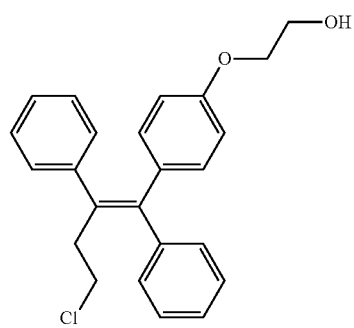

and pharmaceutically acceptable salts thereof, the process comprising:
(a) providing an isomeric mixture of Z,E-4-(4-hydroxy-1,2-diphenylbut-1-enyl)phenol;
(b) separating the desired Z-isomer, a compound of formula IIa, or a salt thereof and the undesired E-isomer, a compound of formula IIb, or a salt thereof from the isomeric mixture of Z,E-4-(4-hydroxy-1,2-diphenylbut-1-enyl)phenol;

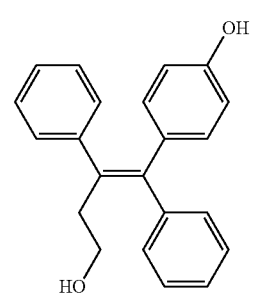

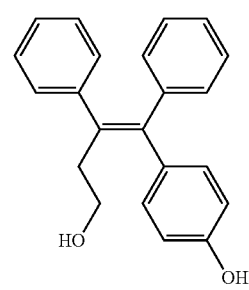

(c) recycling the undesired E-isomer, the compound of formula IIb, or a salt thereof to generate an isomeric mixture of Z,E-4-(4-hydroxy-1,2-diphenylbut-1-enyl)phenol;
(d) optionally, repeating steps (b) and (c);
(e) converting the Z-isomer of 4-(4-hydroxy-1,2-diphenylbut-1-enyl)phenol, the compound of formula IIa, or a salt thereof obtained in step (b) to ospemifene; and wherein the undesired E-isomer, the compound of formula IIb, or a salt thereof is recycled to generate an isomeric mixture of Z,E-4-(4-hydroxy-1,2-diphenylbut-1-enyl)phenol by a process comprising:
(i) providing a solution of the E-isomer, the compound of formula IIb, or a salt thereof, in a solvent;
(ii) stirring and/or heating the solution obtained in step (i) to generate an isomeric mixture of Z,E-4-(4-hydroxy-1,2-diphenylbut-1-enyl)phenol; and (iii) isolating the isomeric mixture of Z,E-4-(4-hydroxy-1,2-diphenylbut-1-enyl)phenol.

2. The process of claim 1, wherein the desired Z-isomer, the compound of formula IIa, or a salt thereof is separated from the undesired E-isomer, the compound of formula IIb, or a salt thereof by a process comprising:

(i) subjecting the isomeric mixture of Z,E-4-(4-hydroxy-1,2-diphenylbut-1-enyl)phenol to treatment with a base in a solvent to generate a reaction mixture;

(ii) separating the desired Z-isomer, the compound of formula IIa, or a salt thereof and the undesired E-isomer, the compound of formula IIb, or a salt thereof from the reaction mixture obtained in step (i); and (iii) optionally, treating the separated Z-isomer, the compound of formula IIa, or a salt thereof and the E-isomer, the compound of formula IIb, or a salt thereof with an acid.

3. The process of claim 2, wherein the desired Z-isomer, the compound of formula IIa, or a salt thereof and the undesired E-isomer, the compound of formula IIb, or a salt thereof are separated from the reaction mixture obtained in step (i), by any of the following:

(x) by carrying out step (i) in a solvent in which one of the isomers, or salt thereof is soluble and the other isomer, or salt thereof is insoluble and precipitates out; or (y) by carrying out step (i) in a solvent and by adding an anti-solvent to it wherein one of the isomers, or salt thereof is precipitated out; or (z) by removing the solvent of step (i) and adding a second solvent to it in which one of the isomers, or salt thereof is soluble and the other isomer, or salt thereof is insoluble and precipitates out.

4. The process of claim 3, wherein the solvent in step (x) is selected from ketones, haloalkanes, hydrocarbons, water, or mixtures thereof.

5. The process of claim 1, wherein the step (ii) is carried out at a temperature in the range of 10° C. to 150° C.

6. The process of claim 1, wherein the step (ii) is carried out until the content of the Z-isomer, the compound of formula IIa, is not less than 48% in the isomeric mixture of Z,E-4-(4-hydroxy-1,2-diphenylbut-1-enyl)phenol.

7. The process of claim 1, wherein the Z-isomer of 4-(4-hydroxy-1,2-diphenylbut-1-enyl)phenol, the compound of formula IIa, or a salt thereof is converted to ospemifene by a process comprising:

(i) reacting the Z-isomer, the compound of formula IIa, or a salt thereof with a compound of formula III,

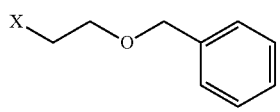

wherein X is selected from the group consisting of Cl, Br, and I, to form a compound of formula IV;

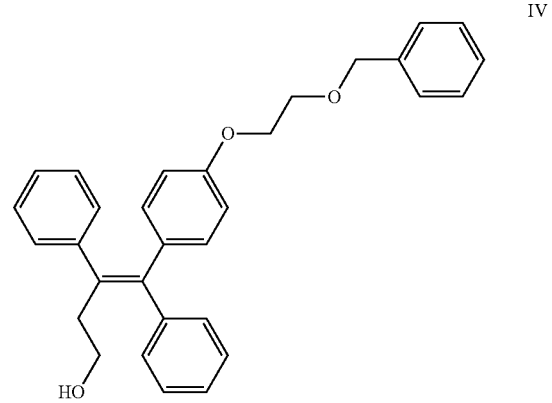 [SMILES: OCC/C(=C(\c1ccccc1)c1ccc(OCCOCc2ccccc2)cc1)c1ccccc1]

(ii) converting the compound of formula IV to a compound of formula V;

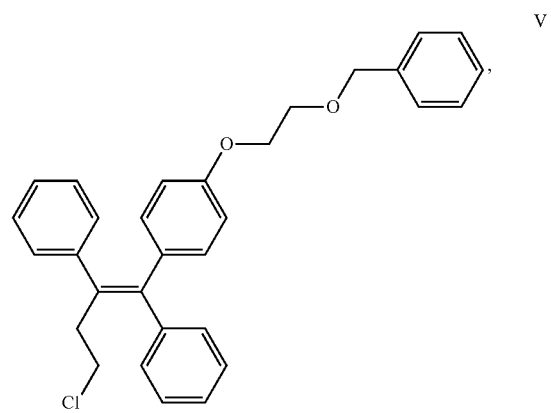 [SMILES: ClCC/C(=C(\c1ccccc1)c1ccc(OCCOCc2ccccc2)cc1)c1ccccc1]

and (iii) deprotecting the compound of formula V to ospemifene.

8. The process of claim 7, wherein the compound of formula IV is converted to the compound of formula V using oxalyl chloride and dimethyl formamide.

9. The process of claim 7, wherein the compound of formula V is deprotected by hydrogenation using a palladium catalyst in the presence of an acid to give ospemifene.

10. The process of claim 1, wherein the level of E-isomer of ospemifene is less than 0.10% w/w with respect to ospemifene, as determined by high performance liquid chromatography (HPLC).

11. The process of claim 7, further comprising the steps of:

(a) providing a solution of ospemifene in a solvent selected from alcohols, nitriles, water, or mixture thereof;

(b) precipitating out ospemifene from the solution obtained in step (a); and (c) isolating the solid formed in step (b) to give ospemifene, having a $D_{50}$ particle size in the range of about 15 microns to about 75 microns and $D_{90}$ particle size in the range of 50 microns to about 150 microns.

12. The process of claim 11, wherein the step (a) is carried out at a temperature in the range of 40° C. to 120° C.

13. The process of claim 11, wherein the step (b) is carried out at a temperature in the range of −5° C. to 30° C.

14. The process of claim 11, wherein the step (b) is carried out without stirring the solution of ospemifene.

* * * * *